United States Patent [19]

Bourk

[11] Patent Number: 5,182,774
[45] Date of Patent: Jan. 26, 1993

[54] NOISE CANCELLATION HEADSET

[75] Inventor: Terrance R. Bourk, San Diego, Calif.

[73] Assignee: Telex Communications, Inc., Minneapolis, Minn.

[21] Appl. No.: 555,990

[22] Filed: Jul. 20, 1990

[51] Int. Cl.$^5$ .............. A61F 11/06; H04R 1/10; H04R 25/00; H04M 1/00
[52] U.S. Cl. ................. 381/71; 381/72; 381/74; 381/183; 381/187; 379/430
[58] Field of Search .............. 379/419, 428, 430; 381/71, 72, 74, 96, 150, 182, 183, 187

[56] References Cited

U.S. PATENT DOCUMENTS

| 2,972,018 | 2/1961 | Hawley et al. | 381/71 |
| 3,629,521 | 12/1971 | Puharich et al. | 381/187 |
| 4,087,653 | 5/1978 | Frieder, Jr. et al. | 379/430 |
| 4,455,675 | 6/1984 | Bose et al. | 381/74 |
| 4,644,581 | 2/1987 | Sapiejewski | 381/183 |
| 4,654,871 | 3/1987 | Chaplin et al. | 381/72 |
| 4,953,217 | 8/1990 | Twiney et al. | 381/72 |

FOREIGN PATENT DOCUMENTS

| 0212840 | 3/1987 | European Pat. Off. | 381/71 |
| 3719963 | 3/1988 | Fed. Rep. of Germany | 381/183 |
| 0066294 | 4/1984 | Japan | 379/430 |

OTHER PUBLICATIONS

Radio Shack, "1990 Catalog", pp. 36,37 Dec., 1989.
Olson, Harry F., "Acoustical Engineering," pp. 414-419.
Dallosta, Patrick Michael, "A Study of Proposed Ear Protection Devices for Low Frequency Noise Attenuation," National Technical Information Service, U.S. Department of Commerce, Apr., 1975, pp. 86-87 117-119.

Primary Examiner—Curtis Kuntz
Assistant Examiner—William Cumming
Attorney, Agent, or Firm—Fredrikson & Byron

[57] ABSTRACT

A headset for acoustic reproduction of an electronic signal which electronic signal is representative of the summation of a desired audio signal and an anti-noise signal. The headset includes a headband, an earcup mounted to the headband, a driver mounted within the earcup which receives and acoustically reproduces the electronic signal, a directional microphone which detects and transduces the acoustical pressure within the earcup cavity, means for generating the anti-noise signal from the microphone signal, and a positioning member for mounting the microphone to the earcup in a position so that the microphone is acoustically coupled to the driver. The microphone is oriented so that its vented or open face is pointing towards the driver. If the driver is provided with an inner dome portion and an outer annulus portion the microphone is positioned by its attachment to a grille plate extending across the driver, the microphone being mounted to the grille plate on a side opposite the driver. The grille plate includes a plurality of apertures, at least one of which is positioned proximate the center of the driver with the microphone mounted across that aperture so that the microphone is acoustically coupled to the dome portion and acoustically isolated from the outer annulus portion.

23 Claims, 3 Drawing Sheets

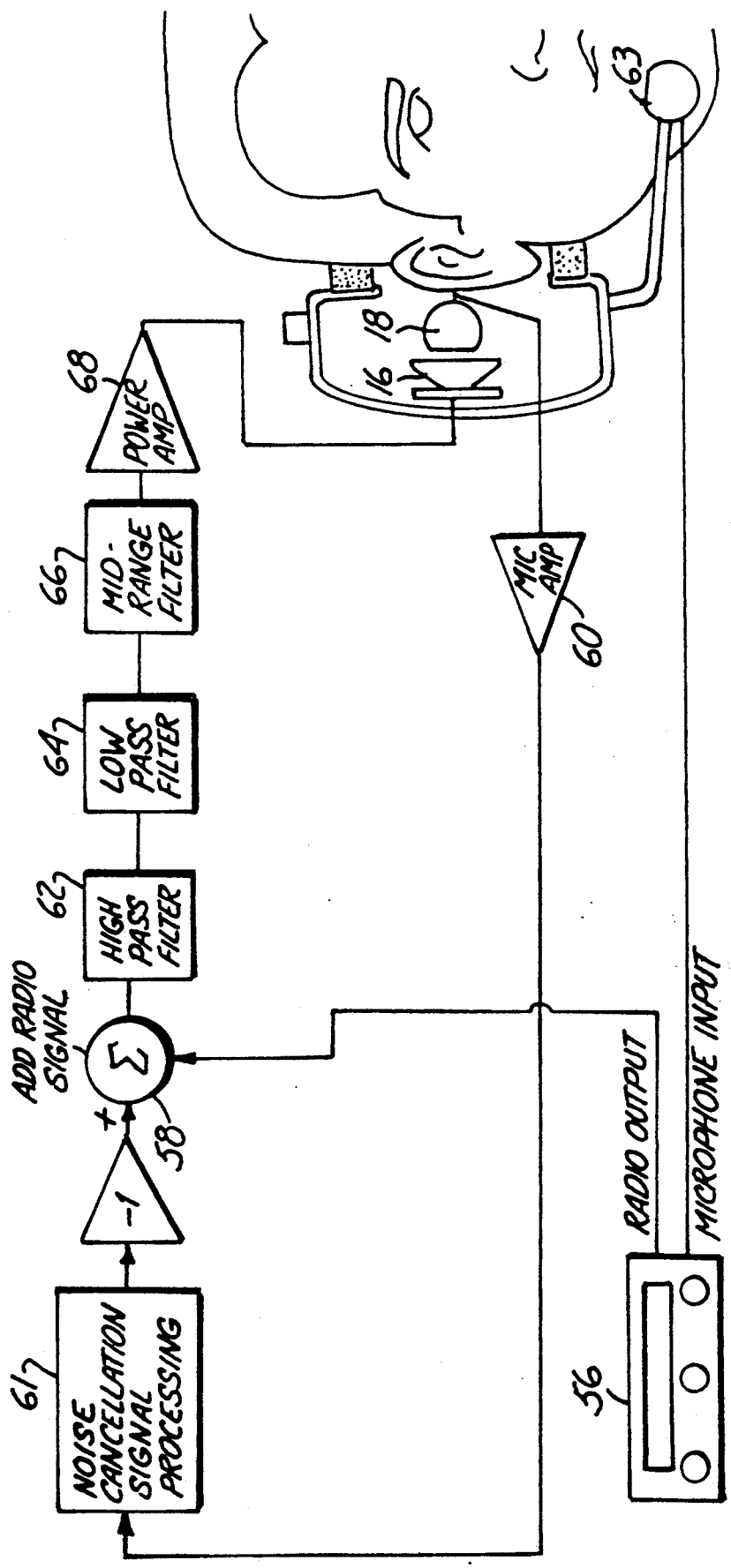

NOISE CANCELLATION HEADSET

FIELD OF THE INVENTION

The present invention relates generally to the field of headsets, and more particularly to headsets which provide for the cancellation of noise during operation.

BACKGROUND OF THE INVENTION

Voice communication between people or with one person located in an environment having significant background or ambient noise can be difficult, and burdensome—in some cases even dangerous if miscommunication occurs. Additionally, working in such an environment can become impossible in some circumstances if there is no shielding of the worker from the noise. As a result of this need to communicate or to shield workers from excessive ambient noise, various devices have been developed.

It has been stated that a typical approach for noise attenuation or shielding in the workplace is to provide workers with headsets having high mass, large internal volume and a spring support that exerts heavy pressure upon the head, i.e. forces the earcup against the head of the wearer. The high mass and heavy pressure operate to create a seal with the wearer's head which in turn serves to attenuate low frequency noise while the large internal volume provides so-called high frequency roll off. The problem with such a passive noise attenuation approach was said to be the discomfort associated with the wearing of such devices.

Other previously described headsets utilized an active noise attenuation approach, wherein a cancellation or anti-noise signal is generated and added to the signal being applied to the headset. Upon being acoustically reproduced, the anti-noise component tends to cancel the background or ambient noise within the region around the ear. Such prior active attenuation techniques are generally of two types, so-called open loop headset systems and closed loop headset systems.

An example of a headset system incorporating open loop components can be found in U.K. Patent Application No. 2,104,754 A - Chaplin, published Mar. 9, 1983, wherein a sensor is used to detect a repetitive noise rate or frequency, which in turn is used by a waveform generator to generate a cancellation signal. The closed loop components depicted in this U.K. application will be discussed more fully below. The problems associated with open loop headset systems are first, they may be limited to only cancelling certain background noise and second, it is difficult to take passive headset attenuation into account. Closed loop headset systems, however, do account for passive attenuation and tend to cancel all background noise.

An early closed loop headset system can be found in Olson, H., Acoustical Engineering, Van Nostrand, New York 1957, pps. 415-418. Subsection C, Headphone-Type Noise Reducer, describes a headset wherein a microphone has been placed in an earcup closely adjacent to a diaphragm for the purpose of providing noise reduction. The microphone senses the pressure in the cavity formed by the earcup on the ear and provides a feedback signal representative of such pressure. It is understood that the pressure in the cavity is reflective of not only the acoustic reproductions of the driver but also external noise which has penetrated the earcup. The microphone signal can be used to cancel or null the external noise by shifting the phase of the signal. Consequently, when acoustically reproduced, the noise component of the microphone signal tends to acoustically cancel external noise present in the cavity.

Another closed loop system can be found in the report AD-A009 274 entitled A STUDY OF PROPOSED EAR PROTECTION DEVICES FOR LOW FREQUENCY NOISE ATTENUATION by P. M. Dallosta dated April, 1975 at pages 86, 87 and 117-119. The report depicts a microphone within an earcup for use in a cancellation circuit. The cancellation circuit is shown at pages 117-119 to sum the communications signal with the microphone signal after the microphone signal has been provided proper gain and phase shift for optimum cancellation. The resultant summed signal is amplified and supplied to the headset.

As indicated above, U.K. Patent Application No. 2,104,745 also discloses closed loop components. Specifically, a microphone is said to be provided closely adjacent a speaker in a headset earphone. The signal from the microphone is fed back to an "adaptive means" which in turn utilizes the microphone signal and the previously described open loop signal to generate a cancellation signal. When the cancellation signal is reproduced by the speaker, it is said that the noise field is nulled except for certain desired sounds. It is also indicated that the microphone signal could be used in a direct feed-back system for attenuating mid-band frequencies.

U.S. Pat. No. 4,455,675 - Bose et al. discloses a closed loop headset system wherein a microphone is mounted coaxially with a driver in a headphone. The open or vented region of the microphone is directed away from the driver and towards the ear canal. The signal generated by the microphone is combined with the signal desired to be reproduced by the driver. Prior to providing the combined signal to the driver, the combined signal is said to be processed by passing it through a compressor to limit the level of high level signals and thereafter it is applied to a compensator to ensure that the open loop gain meets the so-called Nyquist stability criteria to prevent system oscillation.

Somewhat related U.S. Pat. No. 4,644,581 - Sapiejewski discloses a closed loop headset system similar in design to that shown in U.S. Pat. No. 4,455,675 except for two (2) features. Damping material has been positioned to cover the headphone cavity which contains the driver. Also, instead of orienting the microphone coaxially with the driver and directing the open or vented microphone face towards the ear canal, the microphone is located off-set from the driver axis and oriented so that its diaphragm is perpendicular to a plane containing the driver diaphragm, i.e. the open or vented face is directed perpendicular to the driver axis. The perpendicular orientation is said to result in increased bandwidth of the closed loop and the off-set location is said to reduce peaks in frequency response at the high end.

The problem which remains despite these prior open and closed loop headset systems, is that phase lag, particularly at high frequencies, has not been minimized. Such phase lag can occur as a result of several factors, one of which is the propagation delay associated with the distance between the microphone and driver.

SUMMARY OF THE INVENTION

The above described problems are overcome by a headset for acoustic production of an electronic signal which electronic signal is representative of either an anti-noise signal or the summation of a desired audio signal and an anti-noise signal. The headset includes a headband, an earcup mounted to the headband, a driver mounted within the earcup which receives and acoustically reproduces the electronic signal, a microphone which detects and transduces a total acoustic pressure within the earcup, means for generating the anti-noise signal from the microphone signal, and a positioning member for mounting the microphone to the earcup in a position so that the microphone is acoustically closely coupled to the driver. The microphone is oriented so that its vented or open face is pointing towards the driver. Preferably the microphone is mounted so that its diaphragm is as close as possible to the speaker diaphragm, and preferably as close as possible to that portion of the speaker with the best HF performance (so as to result in low phase lag). Preferably, also, the position of the microphone isolates it as much as possible from out of phase acoustic reflections and mechanical standing waves. In a Particularly preferred embodiment, if the driver is provided with an inner dome portion and an outer annulus portion the microphone is positioned by its attachment to a grille plate extending across the driver, and the microphone is mounted to the grille plate on a side opposite the driver. The grille plate includes a plurality of apertures wherein at least one aperture is positioned proximate the center of the driver; the microphone is mounted across that aperture so that the microphone is acoustically coupled to the dome portion and acoustically substantially isolated from the outer annulus portion.

These and other objects and advantages of the invention will become more apparent from the following detailed description when taken in conjunction with the following drawings.

BRIEF DESCRIPTION OF THE DRAWINGS

FIG. 4 is a block diagram of the circuit depicted generally in FIG. 1.

DETAILED DESCRIPTION OF THE PREFERRED EMBODIMENT

Figure 1:
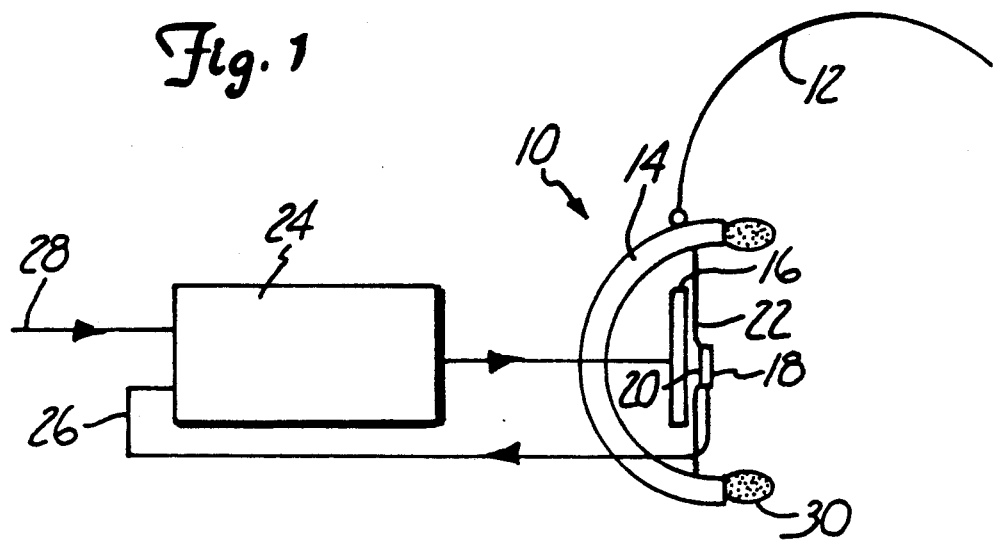
FIG. 1 is a diagrammatic view of a headset according to the present invention.

As will be more completely described with regard to the figures, the present invention is embodied in a new and novel headset system shown in FIG. 1 and generally designated 10. It will be noted that only the right side of the headset is shown and described, since the right and left side are mirror images of each other.

Headset 10 is shown to include headband 12, earcup 14 which is mounted in any known manner to headband 12, driver 16 mounted within earcup 14 which receives and acoustically reproduces desired electronic signals, and microphone 18 having a vented face 20. Microphone 18 generates a signal representative of the acoustic reproductions from driver 16 and background or ambient noise which enters the cavity formed between earcup 14 and the wearer. Microphone 18 is attached to grille plate 22 by any appropriate means so that microphone 18 is centrally positioned over driver 16 and wherein vented face 20 is oriented to point towards driver 16. As will become apparent in relation to FIGS. 2 and 3, microphone 18 is positioned in relation to driver 16 so that it is acoustically closely coupled thereto. Grille plate 22 is attached to earcup 14 and extends across the front face of driver 16. In the preferred embodiment, microphone 18 is a standard electret microphone such as a Knowles 1759.

As indicated above, the signal generated by microphone 18 is provided to electronic circuit 24, at input 26. Electronic circuit 24 processes the desired audio signal provided at input 28, and generates a modified signal for acoustical reproduction by the headset. The modified signal is generated by summing the original audio signal (if any) and an anti-noise signal that is generated based on the signal obtained from microphone 18. The modified signal is thereafter provided to driver 16. Since the anti-noise signal is added to the original audio signal, a portion of the modified signal reproduced by driver 16 will have the effect or tendency to cancel or null background noise in the earcup cavity; also, if the frequency response of the microphone is relatively linear the microphone may detect distortion caused by the speaker as noise and effectively reduce or cancel such distortion as well. As will be more particularly described in relation to FIG. 4, the modified signal may be passed through a plurality of cascaded filters for accentuating a desired frequency range prior to being provided to driver 16.

Figure 2:
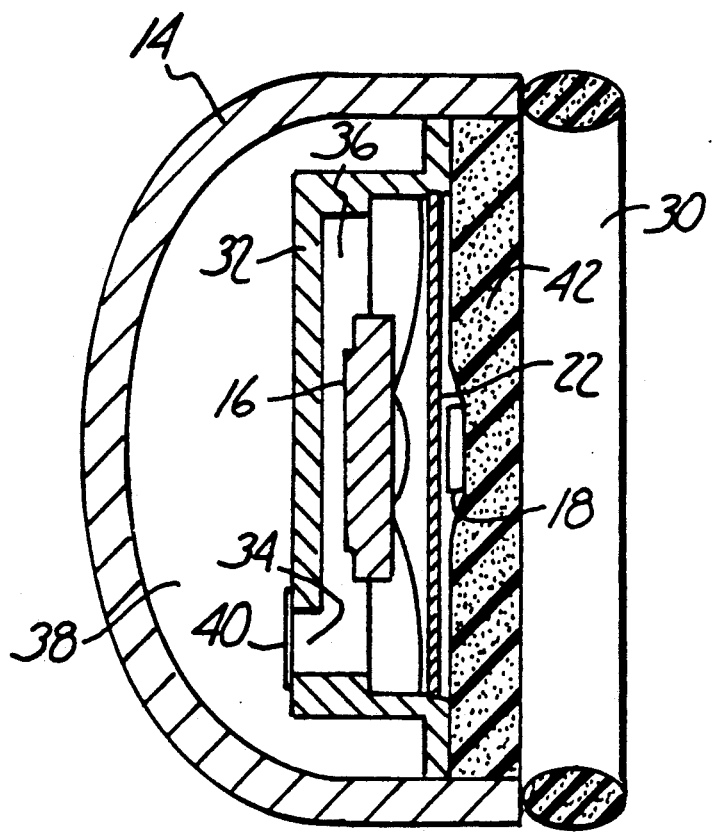
FIG. 2 is a section view of the right earcup of the headset shown in FIG. 1.

Referring now to FIG. 2, earcup 14 is shown to have an ear cushion 30 secured to its outer edge. As will be understood, the force resulting from earcup 14 being pressed against the wearer's head will cause cushion 30 to conform to the shape of the head thereby creating an acoustical seal, contributing some passive noise attenuation capability to the headset. Many of such cushions are known and any would be suitable for the purposes of the present invention.

Driver 16 is shown to be generally centrally mounted within earcup 14 by mounting bracket 32. In the preferred embodiment, the driver 16 may be secured by suitable means such as adhesives into bracket 32; alternately they could be integrally formed. In either case, a secure attachment of the bracket and driver optimizes the so-called electrical-to-acoustical transfer function and prevents front to back acoustic leaks which could limit low frequency response. In order to control rear loading a hole 34 is provided in bracket 32 providing fluid communication between bracket cavity 36 formed between driver 16 and bracket 32 and earcup cavity 38 formed between earcup 14 and bracket 32. Such rear loading is further controlled through the attachment of acoustical cloth 40 over hole 34. Foam overlay 42 is positioned in the open end of earcup 14 to provide further control of the overall phase characteristic of the headset. Foam overlay 42 damps acoustic resonant frequencies above 1 kHz, reducing the magnitude fluctuations, keeping the phase from exhibiting a phase drop at approximately 1.5 kHz, and reducing undesirable high frequency phase variations.

Figure 3:
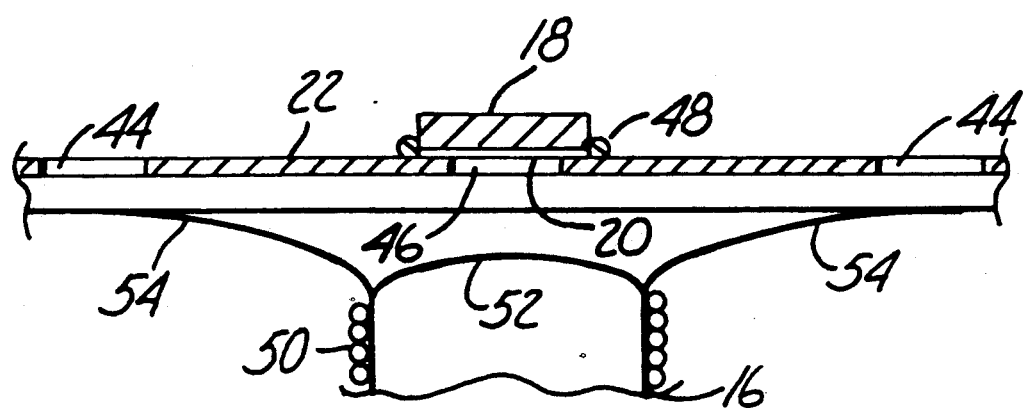
FIG. 3 is an enlarged view of a portion of the earcup shown in FIG. 2.

Referring now to FIG. 3, microphone 18 is shown to be generally coaxially mounted with respect to driver 16. Microphone 18 is mounted in such a position by its attachment to the center of grille plate 22. Grille plate 22 is provided with a number of apertures 44 spaced about the center of grille plate 22 in any desired pattern to optimize coupling, low delay from electrical input to mic output, and minimum acoustic/mechanical standing waves. In a preferred embodiment the grille plate 22 has a central aperture 46 which is positioned directly over the center of driver 16 when grille plate 22 is mounted within earcup 14. Microphone 18 is mounted across aperture 46 so that its vented or open face 20 is pointing through the central aperture 46. Microphone 18 is shown to be held in place by a bead of adhesive 48.

As shown in FIG. 3, driver 16 includes a coil portion 50, a central dome portion 52 and an outer annulus portion 54. The distance between microphone 18 and driver 16 is desirably less than one-quarter inch--preferably less than about one eighth of an inch. The larger the separation between microphone 18 and driver 20 the larger the phase lag resulting in the headset system—the separation must be small in comparison to the wavelengths corresponding to frequencies of interest to avoid excessive Phase lag. Orienting microphone 18 in the described fashion is such that microphone 18 becomes closely acoustically coupled to driver 16, resulting in a minimum phase lag. By interposing grille plate 22 between driver 16 and microphone 18 so that microphone 18 is pointing through central aperture 46, microphone 18 becomes closely coupled to dome portion 52 and substantially acoustically isolated from outer annulus portion 54.

The importance of acoustically coupling microphone 18 to driver 16 and more particularly to dome portion 52 lies in that such coupling causes a sharp 60° to 90° phase lead for signal frequencies occurring at approximately 1.5 kHz. This phase lead results in the headset system having relatively flat phase characteristics from about 1 kHz to about 2.3 kHz. Consequently, the phase compensation electronics can be designed relative to the dominant headset resonance which will cause a rapid drop in the phase characteristics. In relation to the previously described headset system such rapid drop occurs at some point between approximately 2.5 kHz and 3 kHz.

By mounting microphone 18 to grille plate 22 on a side opposite driver 16, microphone 18 is acoustically substantially isolated from outer annulus portion 54. The importance of isolation from outer portion 54 lies in that the outer portion of the driver diaphragm will break up into higher modes of vibration and give rise to large phase shifts at frequencies above 1 kHz, i.e. phase shifts of about 90° to 180°.

As indicated above, the electronic signal provided to driver 16 is generated by summing the anti-noise signal (derived from the microphone signal) with the desired audio signal (if any—the noise cancellation operates whether or not any such audio signal is provided). As shown in FIG. 4, the desired audio signal from a communications radio 56 or similar source is provided to one of the positive inputs of summing circuit 58. The signal detected at the microphone 18 is passed through mic amp 60, passed to a noise cancellation signal processing unit 61 (described below), and then inverted to create the anti-noise signal which is applied to the other positive input of summing circuit 58 (alternately, the signal may merely be inverted by providing it to a negative input of the summing circuit).

The amplifier 60 and equivalent components in the communications radio 56 may be adjusted with respect to one another to set the relative levels of the desired audio and anti-noise signals. A standard microphone 63 may also be provided on the headset to receive and transmit speech of the headset wearer to the communications radio 56.

The total acoustic pressure transduced by the earcup microphone 18 is a combination of the acoustic output of the driver 16 and external ambient noise that has penetrated into the cavity formed between earcup 14 and the wearer. (In the preferred embodiment the headset is a conventional passive noise attenuating headset; such headsets do an acceptable job at attenuating higher frequency noise, but are not as effective at attenuating some strong components of, e.g., aircraft motor and wind noise that occurs at frequencies below about 300 Hz.) The electric signal from the microphone 18 is amplified by mic amp 60 and provided to noise cancellation signal processing unit 61.

The resulting noise signal is then inverted to provide an anti-noise signal that may be amplified and provided to the driver to cancel the detected noise in the headset. This cancellation is effective whether or not an additional radio communication signal (or similar signal) is also provided to the driver.

The aggregate signal transfer characteristic of 60, 61 and 68, as depicted in circuit 24, can be manipulated by choosing the transfer characteristic of unit 61 to provide phase/magnitude compensation which maintain the closed loop characteristics stable with an as large as possible open loop gain in the audio frequency range. The compensation must deal with both low and high frequency instabilities. To this end the modified audio signal, generated by the summation with the anti-noise signal, may be further processed before it is amplified and presented to driver 16. The modified audio signal may be processed by its passage through a plurality of cascaded filters designed to accentuate a desired frequency range while minimizing undesirable phase characteristics. The exact parameter values of each filter are dependent upon the particular driver, microphone and other acoustic elements chosen for a given headset system.

As shown in FIG. 4, the series of cascaded filters may include a high pass filter 62 for filtering out those components of the modified audio signal having frequencies below a first frequency, and a low pass filter 64 for filtering out those components of the modified audio signal having frequencies above a second frequency. In the preferred embodiment the first frequency is in a range extending from 17 to 70 Hz and the second frequency is also in a range extending from 150 Hz to 8 kHz. It should be understood that in filter 62 frequency components of the modified audio signal falling below 17 Hz will be attenuated by a fixed amount and that attenuation of the modified audio signal will decrease linearly for frequency components falling between 17 Hz to 70 Hz at which no attenuation takes place. Similarly, in filter 64 frequency components of the modified audio signal falling above 8 kHz will be attenuated by a fixed amount and that attenuation of the modified audio signal increases linearly for frequency components falling between 150 Hz and 8 kHz at which maximum attenuation takes place. The 8 kHz value, a so-called pole, was chosen for the preferred embodiment to minimize phase lag around the frequency of 2.5 kHz.

The series of filters may also include a mid-range filter 66 for providing additional attenuation to those components of the modified audio signal having frequencies falling between a third and fourth frequency. In the preferred embodiment, the third frequency is 600 Hz and the fourth frequency is 1200 Hz. The centering of this range at 850 Hz provides a second order roll-off in a range where some phase lag can be tolerated.

The filtered modified audio signal is then provided to power amplifier 68 for amplification to a level appropriate for driver 16.

As a result of the above described invention, background or ambient noise reduction within the earcup as a function of frequency is predictable from the open loop frequency response of the headset system. Maximum noise reduction will occur at frequencies from about 30 Hz to about 200 Hz at values of approximately 15 to 28 dB. Above and below the 30 to 200 Hz frequency range, noise reduction falls off according to characteristics determined by the selection of filter parameters. Conventional passive noise reduction built into the headset, however, provides fairly effective noise reduction at higher frequencies, making the headset quite effective in achieving the desired overall reduction of noise, particularly for aircraft applications.

While the invention has been described and illustrated with reference to specific embodiments, those skilled in the art will recognize that modification and variations may be made without departing from the principles of the invention as described herein above and set forth in the following claims.

What is claimed is:

1. A headset for acoustic reproduction of an electronic anti-noise signal, the headset comprising:
    a headband;
    a cup, mounted to the headband;
    a driver mounted within the cup, which receives and acoustically reproduces the electronic signal;
    a microphone, having a directional sensing surface which detects and transduces acoustic pressure within the cup to a corresponding microphone electrical signal;
    means for generating the anti-noise signal from the microphone signal; and
    portioning means for mounting the microphone to the cup and for centering the microphone over the driver with the directional sensing surface oriented substantially directly toward the driver the positioning means comprising a grille plate mounted to the cup across the driver, the microphone being mounted to the grille plate.

2. The headset of claim 1, wherein the grille plate includes a plurality of apertures therethrough, at least one aperture being positioned proximate the center of the driver and the microphone being mounted across such aperture.

3. The headset of claim 2, wherein the microphone is mounted so that the directional sensing surface is pointing through the at least one aperture toward the driver.

4. The headset of claim 3, wherein the distance separating the microphone from the driver is less than about one quarter (¼) of an inch.

5. The headset of claim 2, wherein the apertures are round.

6. The headset of claim 1, further comprising mounting bracket mounted in the cup, the driver being mounted on the mounting bracket.

7. The headset of claim 6, wherein the mounting bracket defines a bracket cavity within the cup and wherein the driver is mounted within the bracket cavity.

8. The headset of claim 7, wherein the mounting bracket is secured within the cup thereby defining an earcup cavity so that the volume of the earcup cavity is sealed from the air outside of the cup.

9. The headset of claim 1, further comprising a foam layer attached to the cup covering the driver and the microphone.

10. The headset of claim 1, further comprising a soft cushion mounted on the outer edge of the cup so that when the cup is pressed on the head of a user, the cushion is between the cup and the user's head.

11. The headset of claim 1, further comprising a second cup, mounted to the headband; a second driver, mounted within the second cup, which receives and acoustically reproduces the electronic signal; a second microphone having a directional sensing surface,; and second positioning means for mounting the second microphone to the second cup and for centering the second microphone over the second driver, wherein the directional sensing surface is oriented directly toward the second driver.

12. The headset of claim 1, including means for summing a desired audio communications signal with the anti-noise signal before providing the anti-noise signal to the driver so that the sum of the desired audio signal and the anti-noise signal and the anti-noise signal is provided to the driver.

13. The headset of claim 12, further comprising a plurality of cascaded filters for accentuating a desired frequency range.

14. The headset of claim 13, wherein the cascaded filters includes a high pass filter for filtering out those components of the electronic signal having frequencies below a first frequency, and a low pass filter for filtering out those components of the electronic signal having frequencies above a second frequency.

15. The headset of claim 14, further comprising a mid-range filter for providing additional attenuation to those components of the electronic signal having frequencies falling between a third and fourth frequency.

16. The headset of claim 15, wherein the first frequency is 17 Hz, the second frequency is 8 kHz, the third frequency is 600 Hz and the forth frequency is 1200 Hz.

17. The headset of claim 7, wherein the driver is sealingly mounted within the mounting bracket.

18. A headset for acoustic reproduction of an electronic anti-noise signal, the headset comprising:
    a headband;
    a cup, mounted to the headband;
    a mounting bracket mounted in the cup, the mounting bracket defining a bracket cavity within the cup on one side of the bracket, the mounting bracket being secured within the cup to define with the cup an earcup cavity so that the volume of the earcup cavity is sealed from air outside of the cup;
    the mounting bracket further containing a bore, thereby providing fluid communication between the earcup cavity and the bracket cavity;
    a driver, which receives and acoustically reproduces the electronic signal, mounted on the mounting bracket with in the bracket cavity;
    a microphone, having a directional sensing surface which detects and transduces acoustic pressure within the cup to a corresponding microphone electrical signal;
    means for generating the anti-noise signal for the microphone signal;
    positioning means for mounting the microphone to the cup and for centering the microphone over the driver with the directional sensing surface oriented substantially directly toward the driver.

19. The headset of claim 18, further comprising a cloth attached to the mounting bracket to cover the bore.

20. A headset for acoustic reproduction of an electronic signal which electronic signal is representative of the summation of an audio signal and an anti-noise signal, the headset comprising:
   a headband;
   a cup, mounted to the headband;
   a driver, mounted within the cup, which receives and acoustically reproduces the electronic signal;
   a directional microphone having a vented face;
   means for generating the anti-noise signal from the microphone signal;
   a grille plate mounted to the cup across the driver, the grille plate including a plurality of apertures therethrough, at least one such aperture being positioned proximate the center of the driver, the microphone being mounted to the grille plate with the vented face of the microphone being mounted across such central aperture with the vented face pointing therethrough oriented substantially directly toward the driver.

21. A headset for acoustic reproduction of an electronic signal which electronic signal is representative of the summation of an audio signal and an anti-noise signal, the headset comprising:
   a headband;
   a cup, mounted to the headband;
   a driver, mounted within the cup, which receives and acoustically reproduces the electronic signal, the driver having an inner dome portion and an outer annulus portion;
   a directional microphone having a vented face;
   means for generating the anti-noise signal from the microphone signal; and
   positioning means for mounting the microphone to the cup so that the microphone is acoustically coupled to the dome portion and isolated from the outer annulus portion, the positioning means comprising a grille plate mounted to the cup across the driver, the microphone being mounted to the grille plate on a side opposite the driver.

22. The headset of claim 21, wherein the grille plate includes a plurality of apertures therethrough, wherein at least one aperture is positioned proximate the center of the driver and wherein the microphone is mounted across the at least one aperture.

23. The headset of claim 22, wherein the microphone is mounted so that the vented face is pointing through the at least one aperture.

* * * * *